United States Patent
Mbaraka et al.

(10) Patent No.: US 10,808,999 B2
(45) Date of Patent: Oct. 20, 2020

(54) PROCESS FOR INCREASING ETHYLENE AND PROPYLENE YIELD FROM A PROPYLENE PLANT

(71) Applicant: Dow Global Technologies LLC, Midland, MI (US)

(72) Inventors: Isa K. Mbaraka, Prospect, KY (US); William L. Jackson, Jr., Baton Rouge, LA (US); Martin A. Cogswell, Camlachie (CA); Mark Siddoway, Friendswood, TX (US); Brien A. Stears, Friendswood, TX (US)

(73) Assignee: Dow Global Technologies LLC, Midland, MI (US)

( * ) Notice: Subject to any disclaimer, the term of this patent is extended or adjusted under 35 U.S.C. 154(b) by 19 days.

(21) Appl. No.: 15/514,272

(22) PCT Filed: Sep. 22, 2015

(86) PCT No.: PCT/US2015/051324
§ 371 (c)(1),
(2) Date: Mar. 24, 2017

(87) PCT Pub. No.: WO2016/053668
PCT Pub. Date: Apr. 7, 2016

(65) Prior Publication Data
US 2017/0248364 A1 Aug. 31, 2017

Related U.S. Application Data

(60) Provisional application No. 62/057,952, filed on Sep. 30, 2014.

(51) Int. Cl.
*F25J 3/02* (2006.01)
*C07C 7/00* (2006.01)
(Continued)

(52) U.S. Cl.
CPC ............ *F25J 3/0219* (2013.01); *C07C 7/005* (2013.01); *C07C 7/04* (2013.01); *C07C 7/09* (2013.01);
(Continued)

(58) Field of Classification Search
CPC ........ F25J 3/0233; F25J 3/0238; F25J 3/0242; F25J 2200/74; F25J 3/0219;
(Continued)

(56) References Cited

U.S. PATENT DOCUMENTS

| | | | | |
|---|---|---|---|---|
| 1,664,412 A | * | 4/1928 | Haynes | F25J 3/0209 62/639 |
| 1,773,012 A | * | 8/1930 | Schuftan | F25J 3/0219 62/625 |

(Continued)

FOREIGN PATENT DOCUMENTS

| | | |
|---|---|---|
| AU | 2005241455 A1 | 11/2005 |
| AU | 2004319953 A1 | 12/2005 |

(Continued)

OTHER PUBLICATIONS

Zimmerman et al., "Ethylene", Ullmann's Encyclopedia of Industrial Chemistry, 2012, Wiley-WCH Verlag GmbH & Co.

(Continued)

*Primary Examiner* — Len Tran
*Assistant Examiner* — Kirstin U Oswald
(74) *Attorney, Agent, or Firm* — Dinsmore & Shohl LLP (57) ABSTRACT

A process for recovery of $C_2$ and $C_3$ components in an on-purpose propylene production system includes utilizing a packed rectifier with a countercurrent stream to strip $C_2$ and $C_3$ components from a combined de-ethanizer overhead lights vapor and cracked gas vapor stream.

7 Claims, 4 Drawing Sheets

(51) Int. Cl.
  *C07C 7/09* (2006.01)
  *C07C 7/04* (2006.01)
(52) U.S. Cl.
  CPC ............ *F25J 3/0233* (2013.01); *F25J 3/0238* (2013.01); *F25J 3/0242* (2013.01); *F25J 2200/02* (2013.01); *F25J 2200/74* (2013.01); *F25J 2205/04* (2013.01); *F25J 2210/02* (2013.01); *F25J 2210/12* (2013.01); *F25J 2215/62* (2013.01); *F25J 2215/64* (2013.01); *F25J 2270/02* (2013.01); *F25J 2270/04* (2013.01)
(58) Field of Classification Search
  CPC .. F25J 2200/02; F25J 2205/04; F25J 2210/02; F25J 2210/12; F25J 2215/62; F25J 2215/64; F25J 2270/02; F25J 2270/04; C07C 7/04; C07C 7/09; C07C 7/005
  USPC .................................................... 62/622, 630
  See application file for complete search history.

(56) References Cited

U.S. PATENT DOCUMENTS

| | | | | |
|---|---|---|---|---|
| 2,028,432 A * | 1/1936 | Barton | C07C 7/04 | 62/628 |
| 2,040,107 A * | 5/1936 | Schlitt | F25J 3/028 | 62/645 |
| 2,213,338 A * | 9/1940 | De Baufre | B01D 3/143 | 62/656 |
| 2,222,275 A * | 11/1940 | Babcock | C07C 7/005 | 208/340 |
| 2,222,276 A * | 11/1940 | Babcock | C10G 5/06 | 62/630 |
| 2,267,761 A * | 12/1941 | Steward | C07C 7/04 | 62/630 |
| 2,271,761 A * | 2/1942 | Coulter | C07C 7/11 | 208/345 |
| 2,573,341 A * | 10/1951 | Kniel | C07C 7/11 | 585/650 |
| 2,601,009 A * | 6/1952 | Swearingen | F25J 3/0209 | 62/625 |
| 2,612,468 A * | 9/1952 | Morrell | C07C 29/84 | 203/53 |
| 2,681,125 A * | 6/1954 | Etherington | B01D 53/12 | 95/36 |
| 2,743,590 A * | 5/1956 | Grunberg | F25J 3/0233 | 62/630 |
| 2,781,293 A * | 2/1957 | Ragatz | C10G 5/04 | 208/344 |
| 2,815,650 A * | 12/1957 | McIntire | F25J 3/0233 | 95/180 |
| 3,130,143 A * | 4/1964 | Salmon | C10G 73/06 | 208/33 |
| 3,192,732 A * | 7/1965 | Cahn | F25J 3/0238 | 62/625 |
| 3,238,735 A * | 3/1966 | Siewert | F25J 3/0242 | 62/623 |
| 3,261,169 A * | 7/1966 | Harmens | F17C 9/04 | 62/623 |
| 3,262,278 A * | 7/1966 | Lynch | F25J 3/0219 | 62/634 |
| 3,318,102 A * | 5/1967 | Henderson | F25J 3/0635 | 62/657 |
| 3,359,743 A * | 12/1967 | Di Napoli | F25J 3/0238 | 62/621 |
| 3,362,175 A * | 1/1968 | Burns | F25J 3/0242 | 62/630 |
| 3,393,527 A * | 7/1968 | Swenson | C10G 5/06 | 62/621 |
| 3,407,613 A * | 10/1968 | Muller | F25J 3/0233 | 62/632 |
| 3,510,534 A * | 5/1970 | Sulzbach | C07C 15/073 | 585/450 |
| 3,516,261 A * | 6/1970 | Hoffman | F25J 3/0209 | 62/622 |
| 3,568,460 A | 3/1971 | Hoffman et al. | | |
| 3,581,511 A * | 6/1971 | Peck | F25J 3/0209 | 62/612 |
| 3,675,435 A * | 7/1972 | Jackson | C07C 7/09 | 62/622 |
| 3,683,634 A * | 8/1972 | Streich | C07C 7/04 | 62/629 |
| 3,721,098 A * | 3/1973 | Forg et al. | F25J 3/0223 | 62/634 |
| 3,929,924 A | 12/1975 | Chapman et al. | | |
| 3,929,925 A | 12/1975 | Chapman et al. | | |
| 4,167,402 A * | 9/1979 | Davis | F25J 3/0247 | 62/630 |
| 4,182,925 A | 1/1980 | Chapman | | |
| 4,192,825 A * | 3/1980 | Chapman | C07C 2/62 | 585/719 |
| 4,217,759 A * | 8/1980 | Shenoy | C01B 3/506 | 252/373 |
| 4,270,940 A | 6/1981 | Rowles et al. | | |
| 4,277,268 A * | 7/1981 | Spangler, Jr. | B01D 1/2856 | 203/24 |
| 4,454,460 A | 6/1984 | Tahara et al. | | |
| 4,456,461 A | 6/1984 | Perez | | |
| 4,511,381 A * | 4/1985 | Mehra | C07C 7/11 | 62/625 |
| 4,556,404 A | 12/1985 | Shenoy et al. | | |
| 4,629,484 A * | 12/1986 | Kister | F25J 3/0219 | 62/622 |
| 4,675,035 A * | 6/1987 | Apffel | F25J 3/0209 | 62/625 |
| 4,714,487 A | 12/1987 | Rowles et al. | | |
| 4,720,293 A * | 1/1988 | Rowles | F25J 3/0238 | 62/630 |
| 4,743,282 A * | 5/1988 | Mehra | C07C 7/11 | 62/625 |
| 4,770,683 A * | 9/1988 | Stothers | F25J 3/0266 | 62/625 |
| 4,854,955 A * | 8/1989 | Campbell | F25J 3/0209 | 62/621 |
| 4,861,360 A * | 8/1989 | Apffel | F25J 3/0209 | 62/625 |
| 4,869,740 A * | 9/1989 | Campbell | C07C 7/04 | 62/621 |
| 4,889,545 A * | 12/1989 | Campbell | C07C 7/04 | 62/621 |
| 4,895,584 A | 1/1990 | Buck et al. | | |
| 4,897,098 A * | 1/1990 | Pate | C07C 7/04 | 62/630 |
| 4,900,347 A * | 2/1990 | McCue, Jr. | F25J 3/0219 | 62/627 |
| 4,940,529 A * | 7/1990 | Beaton | C10G 69/04 | 208/108 |
| 5,035,732 A * | 7/1991 | McCue, Jr. | F25J 3/0219 | 62/627 |
| 5,090,977 A * | 2/1992 | Strack | C10G 70/02 | 208/351 |
| 5,152,148 A | 10/1992 | Crum et al. | | |
| 5,361,589 A | 11/1994 | Howard et al. | | |
| 5,377,490 A * | 1/1995 | Howard | F25J 3/0238 | 62/623 |
| 5,414,168 A | 5/1995 | Scott | | |
| 5,421,167 A | 6/1995 | Verma et al. | | |
| 5,551,972 A | 9/1996 | Wood et al. | | |
| 5,566,554 A | 10/1996 | Vijayaraghavan et al. | | |
| 5,678,424 A * | 10/1997 | Nazar | C07C 7/04 | 62/630 |
| 5,681,908 A * | 10/1997 | Mehra | B01J 8/0035 | 526/68 |
| 5,685,170 A * | 11/1997 | Sorensen | B01D 53/1418 | 62/625 |
| 5,771,712 A * | 6/1998 | Campbell | C07C 7/005 | 62/621 |

(56) References Cited

U.S. PATENT DOCUMENTS

| | | | |
|---|---|---|---|
| 5,791,161 A * | 8/1998 | Manley | C10G 5/06 |
| | | | 62/630 |
| 5,811,621 A * | 9/1998 | van Dijk | B01D 3/009 |
| | | | 203/73 |
| 5,881,569 A * | 3/1999 | Campbell | F25J 3/0209 |
| | | | 62/621 |
| 5,884,504 A * | 3/1999 | Nazar | C07C 7/04 |
| | | | 62/630 |
| 5,890,378 A | 4/1999 | Rambo et al. | |
| 5,953,935 A | 9/1999 | Sorensen et al. | |
| 5,960,643 A * | 10/1999 | Kuechler | C07C 7/005 |
| | | | 62/620 |
| 6,021,647 A * | 2/2000 | Ameringer | F25J 3/0209 |
| | | | 62/631 |
| 6,098,425 A * | 8/2000 | Stothers | F25J 3/0209 |
| | | | 62/621 |
| 6,311,516 B1 | 11/2001 | Key et al. | |
| 6,516,631 B1 * | 2/2003 | Trebble | F25J 3/0209 |
| | | | 62/630 |
| 6,560,989 B1 | 5/2003 | Roberts et al. | |
| 6,578,378 B2 * | 6/2003 | Kaiser | C10G 70/043 |
| | | | 62/622 |
| 6,601,406 B1 * | 8/2003 | Deng | C07C 7/005 |
| | | | 62/621 |
| 6,604,380 B1 | 8/2003 | Reddick et al. | |
| 6,712,880 B2 | 3/2004 | Foglietta et al. | |
| 6,823,692 B1 * | 11/2004 | Patel | F25J 3/0209 |
| | | | 62/620 |
| 7,051,553 B2 | 5/2006 | Mak et al. | |
| 7,207,192 B2 * | 4/2007 | Ronczy | F25J 3/0219 |
| | | | 62/630 |
| 7,437,891 B2 * | 10/2008 | Reyneke | F25J 3/0252 |
| | | | 62/620 |
| 7,565,815 B2 * | 7/2009 | Wilkinson | F25J 3/0238 |
| | | | 62/613 |
| 8,434,325 B2 | 5/2013 | Martinez et al. | |
| 8,840,707 B2 * | 9/2014 | Mak | C10L 3/12 |
| | | | 62/620 |
| 9,296,966 B2 * | 3/2016 | Mak | C10L 3/12 |
| | | | 62/620 |
| 9,777,960 B2 * | 10/2017 | Currence | F25J 3/0209 |
| 2002/0174679 A1 | 11/2002 | Wei | |
| 2002/0198430 A1 | 12/2002 | Kaiser et al. | |
| 2004/0148964 A1 * | 8/2004 | Patel | C07C 7/04 |
| | | | 62/620 |
| 2004/0176646 A1 | 9/2004 | Van Egmond et al. | |
| 2004/0206112 A1 * | 10/2004 | Mak | F25J 3/0233 |
| | | | 62/617 |
| 2005/0005636 A1 * | 1/2005 | Schroeder | F25J 3/0238 |
| | | | 62/620 |
| 2005/0107650 A1 | 5/2005 | Sumner | |
| 2006/0021377 A1 | 2/2006 | Lee et al. | |
| 2006/0021379 A1 * | 2/2006 | Ronczy | F25J 3/0238 |
| | | | 62/620 |
| 2006/0021914 A1 | 2/2006 | Sanchez | |
| 2006/0032269 A1 * | 2/2006 | Cuellar | F25J 3/0233 |
| | | | 62/620 |
| 2006/0042312 A1 | 3/2006 | Winningham | |
| 2006/0283207 A1 * | 12/2006 | Pitman | F25J 3/0233 |
| | | | 62/620 |
| 2007/0007174 A1 * | 1/2007 | Strack | C10G 9/002 |
| | | | 208/106 |
| 2007/0144886 A1 * | 6/2007 | Sylvester | B01D 3/005 |
| | | | 203/19 |
| 2007/0204651 A1 * | 9/2007 | Nanda | F25J 3/0238 |
| | | | 62/620 |
| 2008/0000265 A1 | 1/2008 | Cuellar et al. | |
| 2008/0083246 A1 | 4/2008 | Shah et al. | |
| 2008/0141712 A1 * | 6/2008 | Verma | C07C 7/005 |
| | | | 62/620 |
| 2008/0141713 A1 * | 6/2008 | Verma | C07C 7/005 |
| | | | 62/630 |
| 2008/0190136 A1 * | 8/2008 | Pitman | F25J 3/0209 |
| | | | 62/620 |
| 2009/0100862 A1 * | 4/2009 | Wilkinson | F25J 3/0238 |
| | | | 62/620 |
| 2009/0112037 A1 * | 4/2009 | Reyneke | C07C 7/04 |
| | | | 585/648 |
| 2010/0206003 A1 * | 8/2010 | Mak | F25J 3/0209 |
| | | | 62/630 |
| 2010/0217059 A1 * | 8/2010 | Reyneke | F25J 3/0219 |
| | | | 585/651 |
| 2010/0287985 A1 * | 11/2010 | Martinez | F25J 3/0209 |
| | | | 62/625 |
| 2011/0005273 A1 | 1/2011 | Gahier et al. | |
| 2011/0067441 A1 * | 3/2011 | Martinez | F25J 3/0233 |
| | | | 62/620 |
| 2012/0151962 A1 | 6/2012 | Mualim et al. | |
| 2013/0074542 A1 | 3/2013 | Mehrpooya et al. | |
| 2014/0075987 A1 * | 3/2014 | Mak | F25J 3/0233 |
| | | | 62/630 |
| 2017/0176099 A1 * | 6/2017 | Gaskin | F25J 3/0295 |

FOREIGN PATENT DOCUMENTS

| | | | | |
|---|---|---|---|---|
| AU | 2005285436 A1 | 3/2006 | | |
| AU | 2002338248 B2 | 12/2007 | | |
| CA | 1069817 A1 | 1/1980 | | |
| CA | 2549942 A1 | 12/2006 | | |
| CA | 2511403 A1 | 1/2007 | | |
| CA | 2593886 A1 | 1/2008 | | |
| CA | 2662803 A1 | 1/2008 | | |
| CA | 2667429 A1 | 5/2008 | | |
| CA | 2793469 A1 | 9/2011 | | |
| CN | 1407304 A | 4/2003 | | |
| EP | 0161100 A2 * | 11/1985 | | F25J 3/0247 |
| EP | 0161100 A2 * | 11/1985 | | F25J 3/0209 |
| EP | 825245 A2 | 2/1998 | | |
| GB | 1475475 A | 6/1977 | | |
| GB | 2102931 A | 2/1983 | | |
| GB | 2324536 A | 10/1998 | | |
| RU | 2167188 C1 | 5/2001 | | |
| RU | 2004130481 A | 7/2005 | | |
| WO | 9850742 A1 | 11/1998 | | |
| WO | 2004065868 A2 | 8/2004 | | |
| WO | 2005114076 A1 | 12/2005 | | |
| WO | 2006031362 A1 | 3/2006 | | |
| WO | 2006036441 A1 | 4/2006 | | |
| WO | 2006039172 A2 | 4/2006 | | |
| WO | 2006049515 A1 | 5/2006 | | |
| WO | 2006123240 A1 | 11/2006 | | |
| WO | 2007008254 A1 | 1/2007 | | |
| WO | 2007018517 A1 | 2/2007 | | |
| WO | 2008005518 A2 | 1/2008 | | |
| WO | 2009103715 A2 | 8/2009 | | |
| WO | 2009140070 A1 | 11/2009 | | |
| WO | 2012087740 A1 | 6/2012 | | |
| WO | 2012177749 A2 | 12/2012 | | |
| WO | 2013056267 A1 | 4/2013 | | |

OTHER PUBLICATIONS

International Search Report and Written Opinion pertaining to PCT/US2015/051324 completed Feb. 26, 2016.
International Preliminary Report on Patentability pertaining to PCT/US2015/051324 dated Apr. 4, 2017.
Office Action pertaining to corresponding Russian Patent Application No. 2017112785, dated Mar. 13, 2019.
Shanghai Economic Association, "Theory Basis, Equipment and Technology for Energy Saving and Emission Reduction", pp. 211-212, East China University of Science and Technology Press.
Office Action pertaining to corresponding Chinese Patent Application No. 201580050949.5, dated Sep. 10, 2019.

* cited by examiner

PROCESS FOR INCREASING ETHYLENE AND PROPYLENE YIELD FROM A PROPYLENE PLANT

This invention relates generally to improving yields of ethylene and propylene from an on-purpose propylene plant.

On-purpose propylene plants are known, such as the UOP Oleflex and Lummus Catofin processes. A typical on-purpose propylene plant's product recovery section employing conventional separation apparatus includes interconnected, sequential unit operations as follows: a) quench tower; b) compressor; c) de-ethanizer; d) $C_3$ splitter; and e) depropanizer. Such a plant tends to have high, up to 2% of product, losses of two and three carbon atom hydrocarbons (ethane, ethylene, propane and propylene) into a lower value fuel gas stream. With this typical plant operating at a capacity of 550 kiloton per annum (kta), the loss of two and three carbon atom hydrocarbons approaches 10 kta. At current prices for such hydrocarbons, the losses to fuel gas are over 10 million US dollars per annum.

The separation of C1s and C2's into separate streams from C3+ material is commonly practiced. There is a common use of cryogenic de-methanizer and de-ethanizer and de-propanizer systems in the hydrocarbon fractionation sections of olefin plants as outlined in Ethylene, H. Zimmerman et al, Ullman's Encyclopedia of Industrial Chemistry, Online ISBN: 9783527306732. For a de-methanizer, the feed temperatures can vary but are typically about −100° C. and the pressures are from 400-500 psia. The overhead residual product contains hydrogen, CO, methane, and small amounts of C2's.

De-ethanizers are also known in the art. In front end demethanizer fractionation trains, the demethanizer is typically followed by a deethanizer. The deethanizer will have a concentrated C2 stream used for reflux. For example, U.S. Pat. No. 5,421,167 discloses an enhanced olefin recovery method where a liquid hydrocarbon stream is injected for improved condensation against propylene refrigeration conditions. U.S. Pat. No. 5,152,148 discloses a propane removal process where the depropanizer bottoms are used to reflux the deethanizer to improve propane recovery. U.S. Patent Application Publication 20020198430 discloses a process for purification of ethylene, which provides improved recovery but also uses a demethanizer and deethanizer column. PCT Publication WO2008005518 discloses a propane recovery method where a high pressure feed gas is chilled and expanded to condense the feed gas into an enriched C2+ liquid, which is used for deethanizer reflux.

There are several absorption methods practiced for separating hydrocarbons. For instance, U.S. Pat. No. 5,414,168 describes a process for recovering purified hydrogen; U.S. Patent Application Publication 20020174679 discloses an ethylene plant refrigeration system; and U.S. Pat. No. 6,712,880 describes a cryogenic process utilizing high pressure absorber column.

There are also several methods for separating gases from liquefied natural gas (LNG)—particularly for separating natural gas liquids (NGL, C2 and higher components) from natural gas. For example, U.S. Pat. Nos. 6,604,380 and 8,434,325 describe methods for LNG processing and teach the recovery of NGL's from an LNG stream. U.S. Patent Application Publication 20060042312 describes a process for extracting ethane and heavier hydrocarbons from LNG by extraction of C2+ from LNG using heat exchangers, a fractionating column, and focuses on those processing steps that reduce compression needs. U.S. Patent Application Publication 20080000265 discloses a method which recovers NGL from LNG by splitting feed and allowing some feed and some to heat parts of the fractionator. U.S. Patent Application Publication 20080083246, which uses a gas conditioning method for recovery of C2+ from LNG, teaches a heat integration method utilizing a turbo-compressor/expander.

For recovering NGL's, the typical gas plant will include a de-methanizer and a de-ethanizer. This would fractionate the gas into a residual gas stream, a C2 enriched stream and a C3 enriched stream (the bottoms of the deethanizer). U.S. Pat. No. 7,051,553 teaches a general two column method for NGL recovery. A two-column NGL recovery plant includes an absorber and a distillation column in which the absorber receives two cooled reflux streams, wherein one reflux stream comprises a vapor portion of the NGL and wherein the other reflux stream comprises a lean reflux provided by the overhead of the distillation column. These types of configurations are used for upgrading existing NGL plants and typically exhibit C3 recovery of at least 99% and high C2 (90%) recovery. Other examples include U.S. Pat. Nos. 5,566,554, 4,714,487, 4,456,461, 4,270,940, 4,454,460, WO2009140070, WO2009103715, WO2008005518, WO2006123240, AU2002338248, WO2006031362/ AU2005285436, WO2006049515, and CA2593886.

It is also known to employ a turbo-expander and show the use of a turbo-expander as part of a cryogenic system to recover C2's and C3's separately from the fuel gas. Typically, the separation relies on a demethanizer column, as disclosed for example, in WO2012087740, US20110005273, U.S. Pat. Nos. 5,771,712, 5,890,378, 5,953,935, 6,311,516, 4,869,740, 4,895,584, and WO2013056267, WO2012177749, WO2012087740, WO2004065868, AU2004319953, WO2005114076/ AU2004319953, AU2005241455, WO2006036441, WO2006039172, WO2007008254, CA1069817, CA2511403, CA2549942, CA2662803, CA2667429, GB1475475, GB2102931, GB2324536, U.S. Pat. No. 4,272, 969, US20130074542, and WO1998050742.

There are several improved refrigeration methods which differ from the foregoing disclosure in that they do not use a concentrated C2's stream to rectify an upcoming vapor to allow separation into a fuel gas and C2's steam. Such methods include those disclosed in CA2793469, U.S. Pat. Nos. 3,568,460, 5,361,589, and US20060021377. Other examples that emphasize extraction and off-gas treating differ in the same way include U.S. Pat. No. 4,556,404, AU2005276970, US20120151962, and US20060021914. There are other methods that require a chemical reaction, including for example, those described in EP825245, U.S. Pat. Nos. 3,929,924, 3,929,925, 4,182,925, US20040176646, and US20050107650.

U.S. Pat. No. 5,551,972 (Wood et al.) discloses an absorption process for separating a feed gas stream having components with a spectrum of volatilities ranging from volatile (light) components, intermediate volatility components and least volatile (heavy) components. The process includes three sequential steps. Step one contacts a feed gas stream with an internally generated liquid lean solvent stream in an absorber to produce a light product gas stream composed predominantly of light components contained in the feed stream and a rich solvent stream containing most of the intermediate and heavy components found in the feed stream. An absorption column in which the feed gas flows up the column and has countercurrent contact with an absorption solvent that flows down the column may be used in this step. Step two flashes the rich solvent stream at reduced pressure in a flash zone to produce an intermediate product gas stream composed predominantly of the intermediate components and a lean solvent stream. One or more flash drums connected in series and operating at reduced pressure with no external heat added may be used in this step two. Step three conveys the lean solvent stream from the flash zone to the absorber. The lean solvent stream is composed predominantly of heavy components of the feed stream.

U.S. Pat. No. 5,551,972 teaches an absorption process for separating nitrogen from a natural gas stream and/or recovering hydrogen from a refinery and/or petrochemical gas stream. This teaches using an internal generated solvent. U.S. Pat. No. 5,551,972 teaches generating the solvent used for absorption by flashing the lights from the absorber bottoms stream and consists of the heavy components in the feed stream. This process returns the heavier feed components in the feed stream to the de-ethanizer column and creates a largely C2's stream for reflux from the lighter components in the feed stream by partially condensing the overhead of a packed rectifier. This largely C2's stream is an intermediate stream to the C1− and C3+ streams and is not the heavier components. In addition, the process of U.S. Pat. No. 5,551,972 generates an internal solvent by flashing from the bottoms product. The foregoing invention cools and partially condenses the overhead (lights) of a rectifier to generate the largely C2's stream as a reflux stream for the rectifier.

U.S. Pat. No. 5,771,712 (Campbell et al.) teaches a process for recovering propane, propylene and heavier hydrocarbon components from a hydrocarbon gas stream. The process begins with cooling and/or expanding the hydrocarbon gas stream to partially condense it and then separating the partially condensed stream to provide a first vapor stream. The process continues by directing the first vapor stream into a contacting device to form a third vapor stream and a three carbon atom ($C_3$)-containing liquid stream. Next, the $C_3$-containing stream passes through a distillation column to separate from that stream a second vapor stream that contains a major portion of the $C_3$-containing stream's $C_3$ components and heavier hydrocarbon components. The second vapor stream enters into a heat exchange relation with the third vapor stream to cool the second vapor stream and at least partially condense it and form a condensed stream. At least a portion of the condensed stream passes to and through a contacting device to intimately contact the first vapor stream with the balance of the condensed stream entering a distillation column as its top feed.

BRIEF DESCRIPTION OF THE SEVERAL VIEWS OF THE DRAWINGS

The following detailed description of specific embodiments of the present disclosure can be best understood when read in conjunction with the following drawings, in which.

Figure 1:
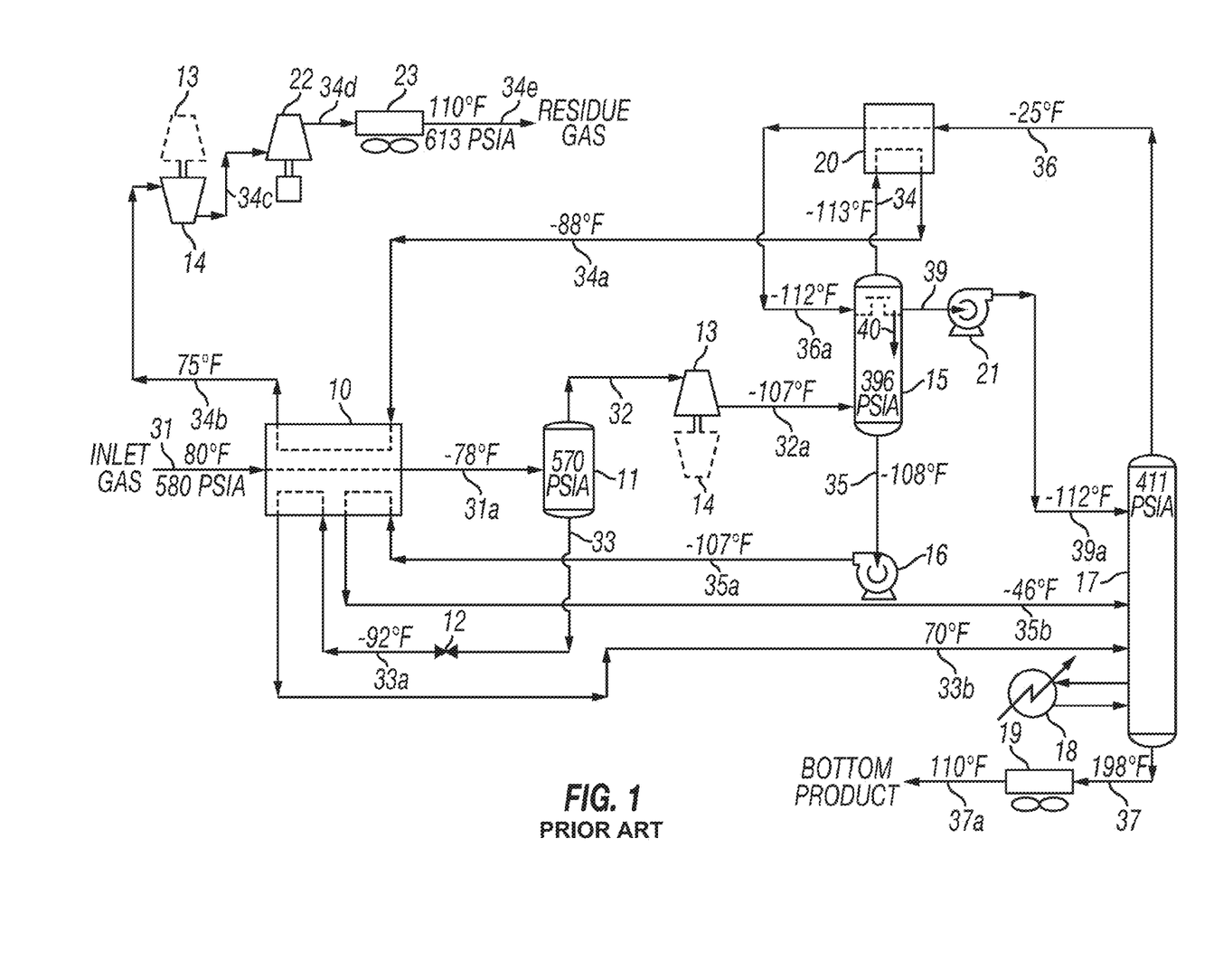
FIG. 1 is a schematic view of a process for upgrading a hydrocarbon-based composition.

FIG. 1 herein reproduces FIG. 4 from Cambell et al (U.S. Pat. No. 5,771,712). In the process shown in FIG. 1, feed gas enters at 80° F. and a pressure of 580 psia as stream 31. The feed stream 31 is cooled in exchanger 10 by heat exchange with cool residue gas at −88° F. (stream 34a), with separator liquids at −92< F. (stream 33a), and with separator/absorber liquids at −107° F. (stream 35a). The cooled stream 31a enters separator 11 at −78° F. and 570 psia where the vapor (stream 32) is separated from the condensed liquid (stream 33).

The vapor (stream 32) from separator 11 enters a work expansion machine 13 in rhich mechanical energy is extracted from this portion of the high pressure feed. The machine 13 expands the vapor substantially isentrupically from a pressure of about 570 psia to a pressure of about 396 psia (the operating pressure of separator/absorber 15), with the work expansion cooling the expanded stream 32a to a temperature of approximately −107° F. The expanded and partially condensed stream 32a enters the lower section of separator/absorber 15. The liquid portion of the expanded stream commingles with liquids falling downward from the absorbing section and the combined liquid stream 35 exits the bottom of separator/absorber 15 at −108° F. The vapor portion of the expanded stream rises upward through the absorbing section and is contacted with cold liquid falling downward to condense and absorb the propane and heavier components.

The combined liquid stream 35 from the bottom of the separator/absorber 15 is routed to heat exchanger 10 by pump 16 where it (stream 35a) is heated as it provides cooling of the incoming feed gas as described earlier. The combined liquid stream is heated to −46° F., partially vaporizing stream 35b before it is supplied as a mid-column feed to deethanizer 17. The separator liquid (stream 33) is flash expanded to slightly above the 411 psia operating pressure of deethanizer 17 by expansion valve 12, cooling stream 33 to −92° F. (stream 33a) before it provides cooling to the incoming feed gas as described earlier. Stream 33b, now at 70° F., then enters deethanizer 17 at a lower mid-column feed point. In the deethanizer, streams 35b and 33b are stripped of their methane and $C_2$ components. The resulting liquid product stream 37 exits the bottom of the deethanizer at 198° F. and is cooled to 110° F. (stream 37a) in heat exchanger 19 before flowing to storage.

The operating pressure in deethanizer 17 is maintained slightly above the operating pressure of separator/absorber 15. This allows the deethanizer overhead vapor (stream 36) to pressure flow through heat exchanger 20 and thence into the upper section of separator/absorber 15. In heat exchanger 20, the deethanizer overhead at −25° F. is directed in heat exchange relation with the overhead (stream 34) from separator/absorber 15, cooling the stream to −112° F. (stream 36a) and partially condensing it. The partially condensed stream is then supplied to the separator section in separator/absorber tower 15 where the condensed liquid is separated from the uncondensed vapor. The uncondensed vapor combines with the vapor rising from the lower absorbing section to form the cold distillation stream 34 leaving the upper region of separator/absorber 15. The condensed liquid is divided into two portions. One portion, stream 40, is routed to the lower absorbing section of separator/absorber 15 as the cold liquid that contacts the vapors rising upward through the absorbing section. The other portion, stream 39, is supplied to deethanizer 17 as reflux by pump 21, with reflux stream 39a flowing to a top feed point on deethanizer 17 at −112° F.

The distillation stream leaving the top of separator/absorber 15 at −113° F. is the cold residue gas stream 34. The residue gas stream passes countercurrently to deethanizer overhead stream 36 in heat exchanger 20 and is warmed to −88° F. (stream 34a) as it provides cooling and partial condensation of the deethanizer overhead stream. The residue gas is further warmed to 75° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

U.S. Pat. No. 5,771,712 teaches a process for recovery of C3+ components from a feed hydrocarbon gas and creates a cooled C3− containing liquid stream. U.S. Pat. No. 5,771,712 teaches feeding an inlet gas, only two products, only a residual gas is created from the overhead of the deethanizer. U.S. Pat. No. 5,771,712 teaches cooling and partially condensing the inlet gas and feeding the partially condensed stream to an absorption column where the vapor passes upward through the column contacting a cold downcoming liquid. However, U.S. Pat. No. 5,771,712 teaches using the same liquid composition (drawn from the same stream) for the reflux to the top of the de-ethanizer as the cold liquid that is used in the absorption column.

U.S. Pat. No. 5,890,378 (Rambo et al.) relates to a process for recovery of ethane, ethylene, propane, propylene and heavier hydrocarbon components from a hydrocarbon gas stream. The process begins by dividing the hydrocarbon gas stream into a first stream and a second stream, with the latter being cooled and expanded to a lower pressure and supplied to a contacting device. The first stream is cooled to condense substantially all of it, expanded to the lower pressure and then used to cool a warmer distillation stream from a distillation column to at least partially condense the distillation stream. At least a portion of the partially condensed distillation stream is directed to the contacting device to intimately contact the expanded second stream and yield a combination of vapors and liquids that are separated from the contacting device, with the liquids being supplied to the distillation column.

U.S. Pat. No. 5,890,378 teaches a process for recovery of C2 and heavier hydrocarbons into a single stream from a hydrocarbon gas stream. This reference only teaches creating two product streams from an inlet gas stream as opposed to three in the present invention. This patent teaches cooling and partial condensation of the overhead de-ethanizer stream but directs this partially condensed de-ethanizer overhead to the absorber column and heating the overhead vapor from the absorber. This reference teaches partially condensing the de-ethanizer overhead and routing the partially condensed liquid to the upper sections of an absorber.

U.S. Pat. No. 6,560,989 (Roberts et al.) relates to a method for the recovery of hydrogen and one or more hydrocarbons having one or more carbon atoms from a feed gas containing hydrogen and the one or more hydrocarbons, which process comprises cooling and partially condensing the feed gas to provide a partially condensed feed; separating the partially condensed feed to provide a first liquid stream enriched in the one or more hydrocarbons and a first vapor stream enriched in hydrogen; further cooling and partially condensing the first vapor stream to provide an intermediate two-phase stream; and separating the intermediate two-phase stream to yield a further-enriched hydrogen stream and a hydrogen-depleted residual hydrocarbon stream. Some or all of the cooling is provided by indirect heat exchange with cold gas refrigerant generated in a closed-loop gas expander refrigeration cycle.

Figure 2:
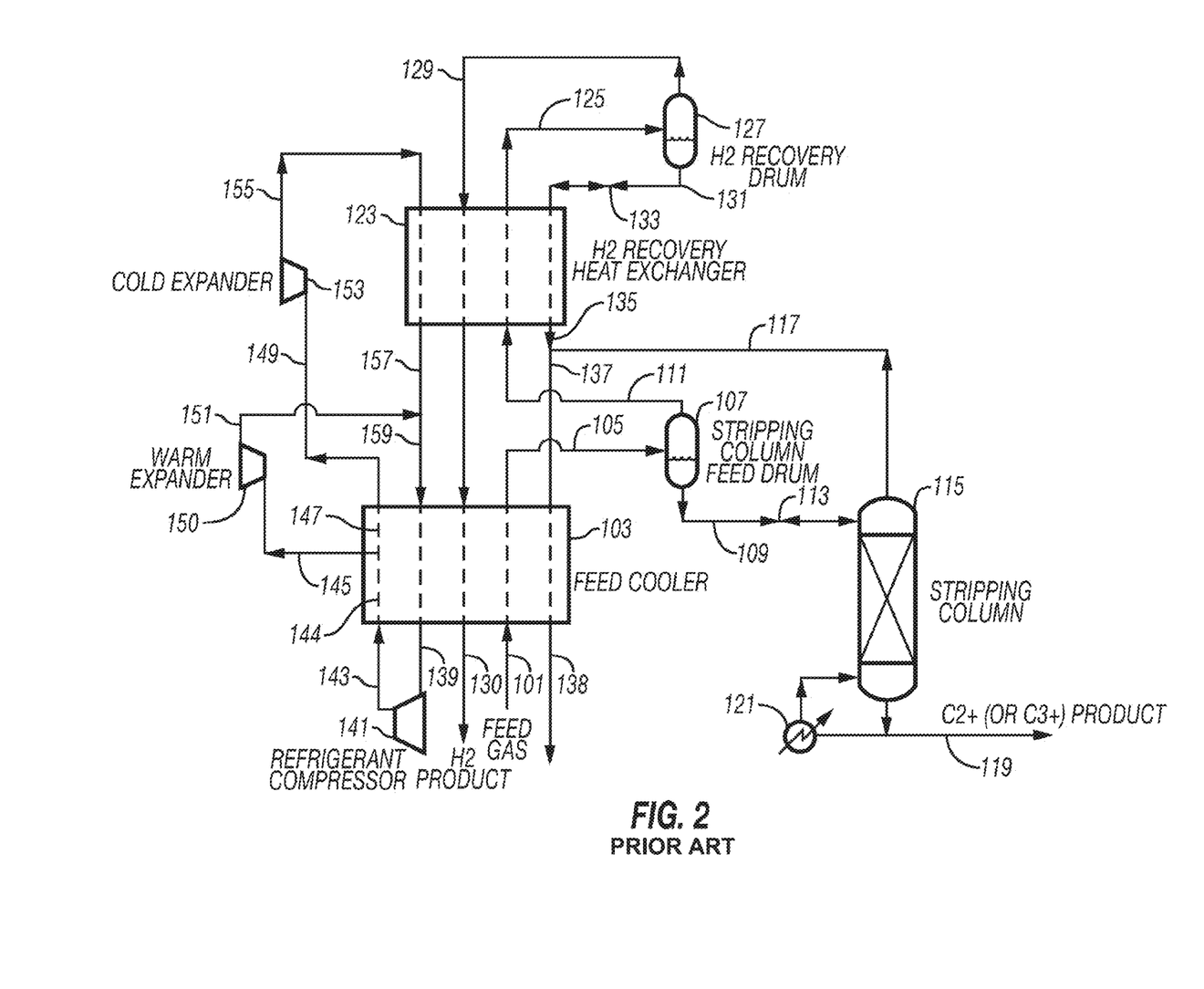
FIG. 2 is a schematic view of a process for upgrading a hydrocarbon-based composition.

FIG. 2 herein reproduces FIG. 1 from Roberts et al. Pretreated feed gas is provided in line 101, typically at a pressure of 100 to 1000 psia and at ambient temperature, and contains hydrogen, one or more light hydrocarbons selected from methane, ethane, ethylene, propane, propylene, and optionally carbon monoxide, nitrogen, and/or $C_4^+$ hydrocarbons. The feed gas is pretreated in an upstream pretreatment step (not shown) to remove water and other components which can freeze out in the downstream processing. The feed gas is cooled and partially condensed in feed cooler or first heat exchange zone 103 by indirect heat exchange with several cold process streams (described later) to yield partially condensed feed in line 105. The partially condensed feed is separated in stripping column feed drum 107 to provide a first liquid stream enriched in hydrocarbons in line 109 and a first vapor stream enriched in hydrogen in line 111.

The first liquid stream may be reduced in pressure across valve 113 and introduced into optional stripping column 115, in which lighter hydrocarbons, residual hydrogen, and other light gases are stripped and withdrawn in overhead line 117. The heavier hydrocarbon fraction is withdrawn as liquid from the bottom of the stripping column via line 119 and contains $C_2^+$ product components such as ethylene and/or propylene. A portion of the stripping column bottoms stream is vaporized in heat exchanger 121 and returned to the column as boilup or stripping vapor. The stripping column typically operates at 50 to 400 psia in the temperature range of −200° F. to +50° F.

The first vapor stream enriched in hydrogen in line 111 is cooled and partially condensed in hydrogen recovery heat exchanger or second heat exchange zone 123 by indirect heat exchange with cold process streams (defined later) to yield a partially condensed stream typically at −200° F. to −300° F. in line 125. The partially condensed stream is separated in hydrogen recovery drum 127 to yield a hydrogen product stream in line 129 and a hydrogen-depleted residual hydrocarbon stream in line 131. The hydrogen product stream in line 129 is warmed in second heat exchange zone 123 by indirect heat exchange to provide a portion of the cooling for the stream entering in line 111, and then is further warmed in first heat exchange zone 103 by indirect heat exchange to provide a portion of the cooling for the feed gas entering in line 101. The final hydrogen product in line 130 is typically at ambient temperature and 15 to 30 psi below the feed gas pressure in line 101. This hydrogen product stream, which typically contains 80 to 97 mole % hydrogen, may be further purified by a pressure swing adsorption or membrane process if desired.

The hydrogen-depleted residual hydrocarbon stream in line 131 may be reduced in pressure across valve 133 and is warmed in second heat exchange zone 123 by indirect heat exchange to provide an additional portion of the cooling for the stream entering in line 111. The warmed stream in line 135 may be combined with the stripped gas stream in line 117, in which case the combined stream in line 137 is further warmed in first heat exchange zone 103 by indirect heat exchange to provide a portion of the cooling for the feed gas entering in line 101. The warmed residual hydrogen-hydrocarbon stream is withdrawn via line 138 and can be used as fuel.

A major portion of the refrigeration for this embodiment is provided by a closed-loop gas expander refrigeration system, refrigerant gas, for example nitrogen, is withdrawn in line 139 from first heat exchange zone 103 and compressed to 600 to 1500 psia in refrigerant compressor 141. Other refrigerants may be used such as, for example, methane, a mixture of nitrogen and methane, or air. The compressed refrigerant gas is cooled in passage 144 of first heat exchange zone 103 to provide a cooled compressed refrigerant gas, which is divided into a first refrigerant gas stream withdrawn in line 145 and a second refrigerant gas stream in heat exchanger passage 147. The second refrigerant gas stream is further cooled in heat exchanger passage 147 to provide cooled refrigerant gas in line 149.

The first refrigerant gas stream in line 145 is work expanded in warm expander 150 to provided a cooled work-expanded refrigerant gas stream in line 151. The further cooled refrigerant gas in line 149 is work expanded in cold expander 153 to provide a cooled reduced-pressure refrigerant gas stream in line 155. Alternatively, instead of work expansion, the gas in line 149 can be reduced in pressure and cooled by Joule-Thomson expansion across a throttling valve (not shown). The cooled reduced-pressure refrigerant gas stream in line 155 is warmed in second heat exchange zone 123 to provide at least a portion of the cooling of the stream entering in line 111, thereby providing a warmed reduced-pressure refrigerant gas stream in line 157. The warmed reduced-pressure refrigerant gas stream in line 157 and the warmed work-expanded refrigerant gas stream in line 151 may be combined, in which case the combined stream in line 159 is warmed in first heat exchange zone 103 by indirect heat exchange to provide a portion of the cooling for the feed gas entering via, line 101 and for the refrigerant flowing through passages 144 and 147. This provides a warmed reduced-pressure refrigerant gas stream in line 139 which is the refrigerant gas described above.

In stripping column 115, the first liquid stream in line 109 is separated to produce a light overhead gas stream in line 117 and a $C_2^+$- or $C_3^+$-enriched hydrocarbon product stream line 119 that can be further separated and purified in additional columns if desired. The light overhead gas stream in line 117 from the stripping column can be recovered separately or combined with the hydrogen-depleted residual hydrocarbon stream in line 135 from the hydrogen recover heat exchanger 123 and rewarmed in feed cooler 103 to be recovered as a fuel stream in line 138. Optionally, a refluxed de-methanizer or de-ethanizer column can be utilized in place of stripping column 115 to increase recovery of the desired hydrocarbon products. Alternatively, the first liquid feed stream in line 109 can be recovered directly from feed drum 107 without stripping or distillation, either as a liquid or vapor product that can be rewarmed in feed cooler 103 if desired to recover refrigeration.

Multiple partial condensation stages can be utilized to provide multiple feed streams to the column or to produce separate hydrocarbon products. For example, a $C_3$-rich hydrocarbon product could be produced from a warmer partial condensation stage and a $C_2$-rich hydrocarbon produced from a colder partial condensation stage. Stripping columns or refluxed distillation columns could be added to remove lighter impurities from one or both hydrocarbon products.

Alternatively, if the feed gas is lean in $C_2$ and heavier hydrocarbons, or if no $C_2^+$ hydrocarbon product is desired, only methane and upgraded methane-rich fuel gas would be recovered. Referring to FIG. 1, the upgraded methane-rich fuel gas product could be the hydrogen-depleted hydrocarbon stream in line 131, or the stripped gas stream in line 117 if stripping column 115 is utilized, or a combination of both, as in line 137. If the stripping column is utilized, the bottom liquid stream in line 119 could be vaporized in feed cooler 103 to provide refrigeration therein.

U.S. Pat. No. 6,560,989 teaches a process for the recovery of hydrogen and one or more hydrocarbon streams from a hydrocarbon feed gas containing hydrogen, methane, C2's, C3's, and optionally carbon monoxide, nitrogen, and C4+ hydrocarbons. This reference teaches partially condensing the feed gas into a first residual vapor and a first residual liquid, separating the liquid, and feeding it to the top of a stripping column. U.S. Pat. No. 6,560,989 teaches the direction of the overhead gas from the stripping column to a product fuel gas stream and does not teach cooling and partially condensing this stream to create a liquid reflux from its own partial condensate as in the present invention. This reference also teaches directing the first residual vapor to further cooling and partial condensation and then passing this to a subsequent hydrogen recovery drum creating a second residual liquid and a second residual vapor. The two products from this step, a fuel gas and a hydrogen stream, are directed to product recovery, and the liquid is not used as reflux to a rectifier column.

As used herein, the term "$C_1$ components" means methane as well as lighter gasses such as hydrogen and nitrogen.

As used herein, the term "$C_2$ components" means ethane and ethylene.

As used herein, the term "$C_3$ components" means propane and propylene.

In some aspects, this invention is a process for recovery of $C_2$ and $C_3$ components from an on-purpose propylene plant, the process comprising: (a) cooling a de-ethanizer overhead lights and cracked gas vapor to a temperature at which at least 80 wt % of the vapor is condensed to form a first partial condensate with a first residual vapor; (b) passing the first partial condensate to a bottom portion of a rectifier; (c) passing the first residual vapor up through a packing of the rectifier while contacting the first residual vapor with a countercurrent stream which comprises from 75 to 95 wt % $C_2$ components, from 5 to 25 wt % $C_1$ components and from 0 to 5 wt % $C_3$ components thereby producing a rectifier overhead stream which comprises from 20 to 45 wt % $C_1$ components, from 40 to 60 wt % $C_2$ components and from 0 to 5 wt % $C_3$ components and a rectifier liquid bottom stream; (d) passing the rectifier liquid bottom stream to the de-ethanizer; (e) partially condensing the rectifier overhead stream in one or more heat exchanger stages to cool the rectifier overhead stream to produce a second partial condensate with a second residual vapor which comprises less than 5 wt % $C_2$ components and a first residual liquid which comprises from 75 to 95 wt % $C_2$ components; (f) passing the combined second residual vapor and first residual liquid to a knockout drum to separate the second residual vapor from the first residual liquid; (g) optionally, using the second residual vapor as a fuel gas and/or as a cooling liquid in the one or more heat exchanger stages; (h) passing a first portion of the second residual liquid to a top portion of the packing in the rectifier to serve as the countercurrent stream; and (i) passing a second portion of the second residual liquid to a product recovery system.

In one embodiment of an on purpose propylene plant, the temperature of the de-ethanizer overhead vapor is from 30 to 50° C. To condense at least 80 percent by weight (wt %) of such de-ethanizer overhead light vapor and cracked gas vapor, the vapor is cooled to from −40 to −60° C. in a first step. In another aspect, the de-ethanizer overhead vapor is cooled to −48° C. The de-ethanizer overhead lights vapor and cracked gas vapor is preferably cooled by passing it through three heat exchange stages.

In one aspect, the first step of the process includes cooling the combined de-ethanizer overhead lights vapor and cracked gas vapor to a temperature at which at least 80 percent by weight (wt %) of the de-ethanizer overhead lights vapor and cracked gas vapor is condensed to form a partial condensate with a first residual vapor. All individual values and subranges from at least 80 wt % are included and disclosed herein. For example, the portion of the de-ethanizer overhead lights vapor and cracked gas vapor which is condensed can be at least 80 wt %, or in the alternative, at least 84 wt %, or in the alternative, at least 88 wt %, or in the alternative, at least 90 wt %, or in the alternative, at least 92 wt %, or in the alternative, at least 94 wt %, or in the alternative, at least 96 wt %.

In one aspect, the second step in the process is passing the partial condensate to a bottom portion of a rectifier. The rectifier useful in the disclosed process is a packed bed rectifier. Packed bed rectifiers are known in the art and any such packed bed rectifier may be used. The rectifier may be packed with any typical packed column material, such as rings, saddles, or structured packing. Alternatively, the rectifier could be a tray type column with bubble-cap, sieve, or valve trays 352.

In one aspect, the third step of the process is passing the first residual vapor up through the packing of the rectifier while contacting the first residual vapor with a countercurrent stream which comprises from 75 to 95 wt % $C_2$ components, from 5 to 25 wt % $C_1$ components and from 0 to 5 wt % $C_3$ components. All individual values and subranges from 75 to 95 wt % $C_2$ components in the countercurrent stream are disclosed and included herein. For example, the countercurrent stream may comprise from 75 to 95 wt % $C_2$ components, or in the alternative, from 75 to 90 wt % $C_2$ components, or in the alternative, from 80 to 95 wt % $C_2$ components. All individual values and subranges from 5 to 25 wt % $C_1$ components in the countercurrent stream are included and disclosed herein. For example, the amount of $C_1$ components can be from 5 to 25 wt %, or in the alternative, from 5 to 20 wt %, or in the alternative, from 10 to 25 wt %. All individual values and subranges from 0 to 5 wt % $C_3$ components in the countercurrent stream are disclosed and included herein. For example, the amount of $C_3$ components in the countercurrent stream can be from 0 to 5 wt %, or in the alternative, from 0 to 3 wt %.

Upon passing the first residual vapor up through the packing of the rectifier while contacting the first residual vapor with a countercurrent stream a rectifier overhead stream and a rectifier liquid bottom stream are produced. The rectifier overhead stream comprises from 20 to 45 wt % $C_1$ components, from 40 to 60 wt % $C_2$ components and from 0 to 5 wt % $C_3$ components. All individual values and subranges from 20 to 45 wt % $C_1$ components are included and disclosed herein. For example the amount of $C_1$ components in the rectifier overhead stream can be from 20 to 45 wt %, or in the alternative from 25 to 45 wt %, or in the alternative, from 30 to 45 wt %. All individual values and subranges from 40 to 60 wt % $C_2$ components are included and disclosed herein. For example, the amount of $C_2$ components can be from 40 to 60 wt %, or in the alternative, from 45 to 60 wt %, or in the alternative, from 50 to 60 wt %.

It will be readily understood that the second and third steps are generally practiced simultaneously in the on purpose propylene plant. However, if the second and third steps are not completed simultaneously, the order in which they are accomplished is not an integral aspect of the disclosed process. That is, the second step may be operated prior to the third step or vice versa.

Figure 4:
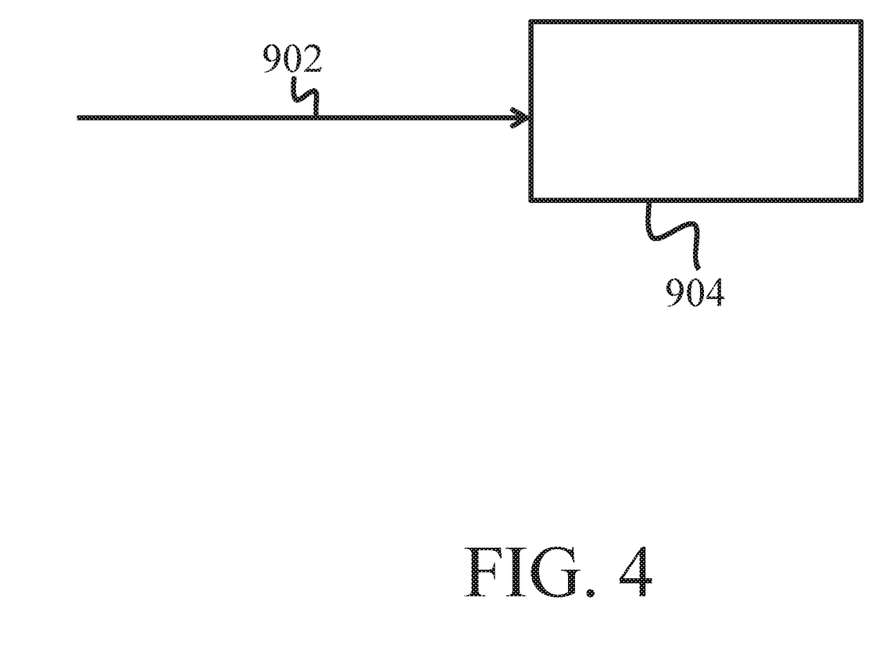
FIG. 4 is a schematic view of a process for upgrading a hydrocarbon-based composition, according to the present embodiments.

In one aspect as shown in FIG. 4, a schematic, a fourth step in the process is passing the rectifier liquid bottom stream 902 to the de-ethanizer 904. In a particular aspect, the rectifier liquid bottom stream 902 is used in the de-ethanizer 904 as a reflux stream.

In one aspect, a fifth step in the process is partially condensing the rectifier overhead stream in one or more heat exchanger stages to cool the rectifier overhead stream to produce a partial condensate with a second residual vapor which comprises less than 5 wt % $C_2$ components and a first residual liquid which comprises from 75 to 95% $C_2$ components. All individual values and subranges from less than 5 wt % $C_2$ components in the second residual vapor are included and disclosed herein. For example, the upper limit of the $C_2$ components in the second residual vapor can be 5 wt %, or in the alternative, 4 wt %, or in the alternative, 3 wt %, or in the alternative 2 wt %, or in the alternative 1 wt %. All individual values and subranges from 75 to 95% $C_2$ components in the first residual liquid herein. For example, the amount of $C_2$ components in the first residual liquid can be from 75 to 95 wt %, or in the alternative, from 80 to 95 wt %.

In one aspect, the one or more heat exchanger stages cool the rectifier overhead stream to a temperature less than or equal to −140° C. All individual values and subrangges of less than or equal to −140° C. are included and disclosed herein. For example, the rectifier overhead stream may be cooled to a temperature less than or equal to −140° C., or in the alternative, less than or equal to −150° C., or in the alternative, less than or equal to −160° C.

It will be readily understood that the fourth and fifth steps are generally practiced simultaneously in the on purpose propylene plant. However, if the fourth and fifth steps are not completed simultaneously, the order in which they are accomplished is not an integral aspect of the disclosed process. That is, the fourth step may be operated prior to the fifth step or vice versa.

In one aspect, a sixth step in the process is passing the combined second residual vapor and first residual liquid to a knockout drum to separate the second residual vapor from the first residual liquid. In a particular aspect, the second residual vapor, following separation, is used as a fuel gas and/or as a cooling liquid in the one or more heat exchanger stages.

In one aspect, a seventh step of the process is passing a first portion of the first residual liquid to a top portion of the packing in the packed bed rectifier to serve as the countercurrent stream.

In one aspect, an eighth step of the process is passing a second portion of the second residual liquid to a product recovery system. In a particular aspect, the second portion of the second residual liquid is passed into a product recovery system of an on-purpose ethylene plant. The on-purpose ethylene plant may, in one aspect, be located proximate to the on purpose propylene production system.

In one aspect, the second residual vapor comprises at least 95 wt % $C_1$ components. All individual values and subranges of at least 95 wt % $C_1$ components are included and disclosed herein. For example, the amount of $C_1$ components in the second residual vapor can be at least 95 wt %, or in the alternative, at least 97 wt %, or in the alternative, at least 99 wt %.

In one aspect, the second residual vapor is first used as a cooling fluid in the one or more heat exchanger stages and is warmed to a temperature of from −50 to −90° C., then subsequently expanded and cooled to a temperature from −110 to −180° C., then used again as a cooling liquid in one or more heat exchanger stages. Methods for expansion and cooling are known, such as by the use of turbo-expanders or Joule-Thompson valves. All individual values and subranges from −50 to −90° C. as the temperature to which the second residual vapor is warmed are included and disclosed herein. For example, the temperature to which the second residual vapor is warmed can be from a lower limit of −90, −80, −70, or −60° C. to an upper limit of −85, −75, −65, −55 or −50° C. For example, the temperature to which the second residual vapor is warmed can be from −50 to −90° C., or in the alternative, from −50 to −75° C., or in the alternative, from −75 to −90° C., or in the alternative, from −60 to −80° C., or in the alternative, from −65 to −85° C. All individual values and subranges from −110 to −180° C. as the temperature to which the second residual vapor is subsequently cooled are included and disclosed herein. For example, the temperature to which the second residual vapor is subsequently cooled can be from a lower limit of −180, −170, −160, −150, −140, −130 or −120° C. to an upper limit of −110, −120, −130, −140, −150, −160, −170 or −175° C. For example, the temperature to which the second residual vapor is subsequently cooled can be from −110 to −180° C., or in the alternative, from −110 to −150° C., or in the alternative, from −150 to −180° C., or in the alternative from −130 to −170° C., or in the alternative, from −140 to −170° C.

Figure 3:
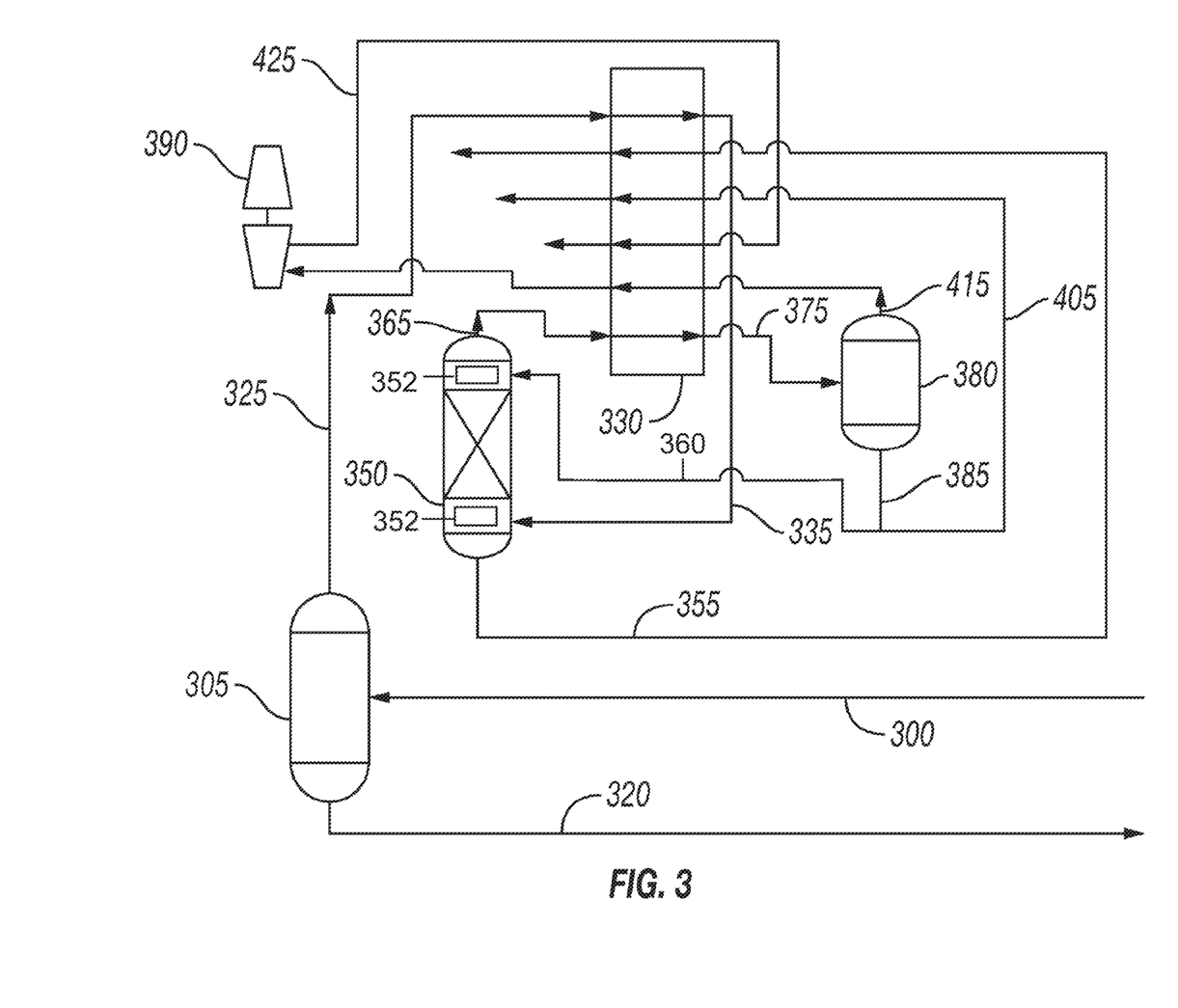
FIG. 3 is a schematic view of a process for upgrading a hydrocarbom-based composition.

FIG. 3 is a schematic illustrating a first embodiment of the process for recovery of $C_2$ and $C_3$ components from an on-purpose propylene plant, as generally disclosed herein. As shown in FIG. 3, the de-ethanizer overhead and the cracked gas vapor streams 300 are fed into knock-out drum 305 as vapor. While shown as a single stream, the de-ethanizer overhead and dried cracked gas may be fed either jointly or separately. A bottoms stream 320 from the knock-out drum 305 is sent back to the de-ethanizer (not shown). The stripped stream 325 is then routed to one or more stages of heat exchanger 330 which cool the stripped stream. The cooled stream 335 is mostly condensed liquid (first partial condensate) but also contains a small vapor fraction (first residual vapor, generally less than or equal to 6 wt %). The cooled stream 335, which is a liquid/vapor stream, is routed to the bottom of a packed bed rectifier 350. The vapor fraction passes up through the packed bed rectifier 350 and is rectified wherein most of the C3's are removed to a bottom liquid stream 355. The liquid stream 355 is pumped back to the de-ethanizer (not shown) as reflux.

As the first residual vapor passes up through the rectifier 350, it is contacted by a countercurrent flow of a $C_2$'s liquid stream 360 at about −145° C. The $C_2$'s liquid stream 360 rectifies the rising first residual vapor removing the heavier components into the bottom liquids stream 355 and therefore concentrating the lights in the vapor stream. This acts to produce a rectifier overhead stream 365.

The rectifier overhead stream 365 is then routed to one or more stages of heat exchanger 330 where it is cooled and partially condensed to about a 39% vapor fraction 375, (forming a second partial condensate). The second partial condensate and vapor stream 375 is then routed to a second knock-out drum 380. About half 360 the liquid bottoms stream 385 from the second knock-out drum 380 is routed to the top of the rectifier 350 and the other half 405 is heated as it is routed to one or more stages of heat exchanger 330. Following heating in the one or more heat exchanger stages, the stream 405 is passed to a $C_2$'s recovery system.

The overhead vapor 415 from the second knock-out drum 380 contains 99% C1's and lighter and is first routed to one or more stages of heat exchanger 330 where it is warmed to about −70° C. After warming in one or more stages of heat exchanger 330, the overhead vapor 415 is expanded in the turbo-expander/compressor 390 from about 400 psia to about 60 psia and cooled to about −150° C. The resulting cold stream 425 from the turbocompressor/expander 390 is then routed to one or more stages of heat exchanger 330, where it is heated to about 40° C. and then used as fuel gas.

What is claimed is:

1. A process for recovery of C2 and C3 components via an on-purpose propylene production system comprising:
cooling a combined vapor stream of a de-ethanizer overhead light vapor from a de-ethanizer and a cracked gas vapor to a temperature at which at least 80 wt % of the combined vapor stream is condensed to form a first partial condensate and a first residual vapor;
passing the first partial condensate to a bottom portion of a rectifier; passing the first residual vapor up through packing of the rectifier while contacting the first residual vapor with a countercurrent stream which comprises from 75 to 95 wt % C2 components, from 5 to 25 wt % Ci components and from 0 to 5 wt % C3 components thereby producing a rectifier overhead stream which comprises from 20 to 45 wt % Ci components, from 40 to 60 wt % C2 components and from 0 to 5 wt % C3 components and a rectifier liquid bottom stream;
passing the rectifier liquid bottom stream to the de-ethanizer;
partially condensing the rectifier overhead stream in one or more heat exchanger stages to cool the rectifier overhead stream to produce a second partial condensate with a second residual vapor which comprises less than 5 wt % C2 components and a first residual liquid which comprises from 75 to 95% C2 components;
passing the combined second residual vapor and first residual liquid to a knockout drum to separate the second residual vapor from the first residual liquid;
passing a first portion of the first residual liquid to a top portion of the packing in the rectifier to serve as the countercurrent stream; and
passing a second portion of the first residual liquid to a product recovery system.

2. The process for recovery of $C_2$ and $C_3$ components according to claim 1, wherein the one or more heat exchanger stages cool the rectifier overhead stream to a temperature less than or equal to −100° C.

3. The process for recovery of $C_2$ and $C_3$ components according to claim 1, wherein the second residual vapor comprises at least 95 wt % $C_1$ components.

4. The process for recovery of $C_2$ and $C_3$ components according to claim 1, wherein the second residual vapor is first used as a cooling medium in the one or more heat exchanger stages and is warmed to a temperature of from −50 to −90° C., then subsequently expanded and cooled to a temperature from −110 to −180° C., then used again as a cooling medium in one or more heat exchanger stages.

5. The process for recovery of $C_2$ and $C_3$ components according to claim 1, wherein the rectifier is a tray type column having a plurality of trays wherein individual trays of the plurality of trays are selected from the group consisting of bubble-cap trays, sieve trays, and valve trays.

6. The process for recovery of $C_2$ and $C_3$ components according to claim 1, using the second residual vapor as at least one of a fuel gas and a cooling medium in the one or more heat exchanger stages.

7. The process for recovery of $C_2$ and $C_3$ components according to claim 1, wherein partially condensing the rectifier overhead stream in the one or more heat exchanger stages to cool the rectifier overhead stream comprises cooling the rectifier overhead stream to a temperature of less than or equal to $-140°$ C.

* * * * *

UNITED STATES PATENT AND TRADEMARK OFFICE
CERTIFICATE OF CORRECTION

Page 1 of 2

PATENT NO. : 10,808,999 B2
APPLICATION NO. : 15/514272
DATED : October 20, 2020
INVENTOR(S) : Isa K. Mbaraka et al.

It is certified that error appears in the above-identified patent and that said Letters Patent is hereby corrected as shown below:

In the Claims

Column 12, Line 14, Claim 1:
"1. A process for recovery of C2 and C3 components via"

Should read:
--1. A process for recovery of $C_2$ and $C_3$ components via--

Column 12, Line 25, Claim 1:
"comprises from 75 to 95 wt% C2 components, from 5"

Should read:
--comprises from 75 to 95 wt% $C_2$ components, from 5--

Column 12, Line 26, Claim 1:
"to 25 wt% Ci components and from 0 to 5 wt% C3"

Should read:
--to 25 wt% $C_1$ components and from 0 to 5 wt% $C_3$--

Column 12, Line 28, Claim 1:
"stream which comprises from 20 to 45 wt% Ci"

Should read:
--stream which comprises from 20 to 45 wt% $C_1$--

Column 12, Line 29, Claim 1:
"components, from 40 to 60 wt% C2 components and"

Signed and Sealed this
First Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,808,999 B2

Should read:
--components, from 40 to 60 wt% $C_2$ components and--

Column 12, Line 30, Claim 1:
"from 0 to 5 wt% C3 components and a rectifier liquid"

Should read:
--from 0 to 5 wt% $C_3$ components and a rectifier liquid--

Column 12, Line 39, Claim 1:
"5 wt% C2 components and a first residual liquid which"

Should read:
--5 wt% $C_2$ components and a first residual liquid which--

Column 12, Line 40, Claim 1:
"comprises from 75 to 95% C2 components;"

Should read:
--comprises from 75 to 95% $C_2$ components;--